US012324903B2

(12) United States Patent
Vogt

(10) Patent No.: US 12,324,903 B2
(45) Date of Patent: *Jun. 10, 2025

(54) BOTULINUM TOXIN PREFILLED PLASTIC SYRINGE

(71) Applicant: Merz Pharma Gmbh & Co. KGaA, Frankfurt am Main (DE)

(72) Inventor: Markus Vogt, Frankfurt am Main (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 859 days.

This patent is subject to a terminal disclaimer.

(21) Appl. No.: 17/534,229

(22) Filed: Nov. 23, 2021

(65) Prior Publication Data

US 2022/0080127 A1 Mar. 17, 2022

Related U.S. Application Data

(63) Continuation of application No. 16/459,382, filed on Jul. 1, 2019, now Pat. No. 11,219,717, which is a continuation of application No. 15/547,941, filed as application No. PCT/EP2015/002600 on Dec. 22, 2015, now Pat. No. 10,406,290.

(30) Foreign Application Priority Data

Feb. 3, 2015 (EP) .................................... 15000310

(51) Int. Cl.
*A61M 5/31* (2006.01)
*A61K 8/64* (2006.01)
*A61K 8/66* (2006.01)
*A61K 9/00* (2006.01)
*A61K 38/48* (2006.01)
*A61K 47/26* (2006.01)
*A61M 5/24* (2006.01)
*A61M 5/315* (2006.01)
*A61M 5/32* (2006.01)
*A61Q 19/08* (2006.01)

(52) U.S. Cl.
CPC ............ *A61M 5/3129* (2013.01); *A61K 8/64* (2013.01); *A61K 8/66* (2013.01); *A61K 9/0019* (2013.01); *A61K 38/4893* (2013.01); *A61K 47/26* (2013.01); *A61M 5/24* (2013.01); *A61M 5/31505* (2013.01); *A61M 5/31513* (2013.01); *A61M 5/3202* (2013.01); *A61Q 19/08* (2013.01); *C12Y 304/24069* (2013.01); *A61K 2800/87* (2013.01); *A61K 2800/91* (2013.01); *A61M 2005/3131* (2013.01); *A61M 2205/0216* (2013.01); *A61M 2205/0222* (2013.01); *A61M 2205/0238* (2013.01); *Y02A 50/30* (2018.01)

(58) Field of Classification Search
CPC .................................................. A61M 5/3129
See application file for complete search history.

(56) References Cited

U.S. PATENT DOCUMENTS

| | | | |
|---|---|---|---|
| 7,829,525 B2 | 11/2010 | Frevert | |
| 8,383,103 B2 | 2/2013 | Gaylis et al. | |
| 8,535,062 B2 | 9/2013 | Nguyen | |
| 8,808,686 B2 | 8/2014 | Del Giudice et al. | |
| 9,554,968 B2 | 1/2017 | Weikart et al. | |
| 9,662,450 B2 | 5/2017 | Jones et al. | |
| 9,827,282 B2 | 11/2017 | Naheed | |
| 9,863,042 B2 | 1/2018 | Jones et al. | |
| 9,937,099 B2 | 4/2018 | Weikart et al. | |
| 9,981,022 B2 | 5/2018 | Hunt | |
| 10,010,362 B2 | 7/2018 | Vogt et al. | |
| 10,017,720 B2 | 7/2018 | Li et al. | |
| 10,039,910 B2 | 8/2018 | Xu | |
| 10,077,415 B2 | 9/2018 | Gohl et al. | |
| 10,119,159 B2 | 11/2018 | O'Keefe | |
| 10,323,218 B2 | 6/2019 | Li et al. | |
| 10,383,510 B2 | 8/2019 | Schutt et al. | |
| 10,406,290 B2 | 9/2019 | Vogt | |
| 10,549,042 B2 | 2/2020 | Vogt | |
| 10,669,512 B2 | 6/2020 | Li et al. | |
| 11,219,717 B2 * | 1/2022 | Vogt ........................ | A61P 17/02 |
| 2006/0269575 A1 | 11/2006 | Hunt | |
| 2007/0134199 A1 | 6/2007 | Frevert | |
| 2008/0045889 A1 | 2/2008 | Gerondale | |
| 2009/0010965 A1 | 1/2009 | Eisele et al. | |
| 2009/0028906 A1 | 1/2009 | Grein et al. | |

(Continued)

FOREIGN PATENT DOCUMENTS

| | | |
|---|---|---|
| CN | 1316906 A | 10/2001 |
| CN | 1826132 A | 8/2006 |

(Continued)

OTHER PUBLICATIONS

International Search Report of International Patent Application No. PCT/EP2015/002600 dated Mar. 14, 2016.
NeuroBloc Scientific Discussion, (2005), http://www.ema.europa.eu/docs/en_GB/docu ment_library/E PAR_-_Scientific_Discussion/human/ 000301/WC500026903.pdf.
PCT Third Party Observation for PCT/EP2015/002600, submitted Oct. 13, 2016.
Dean, D.A. et al., Chapter 12: Sterile products and the role of rubber components. Pharmaceutical Packaging Technology, CRC Press, Jul. 12, 2005, p. 350.
Wortzman, Mitchell S. et al., "The Science and Manufacturing Behind Botulinum Neurotoxin Type A—ABO in Clinical Use", Aesthetic Surgery Journal, Nov./Dec. 2009, vol. 29, No. 6S.

(Continued)

*Primary Examiner* — Albert M Navarro
(74) *Attorney, Agent, or Firm* — McBee Moore & Vanik IP, LLC

(57) ABSTRACT

The present invention relates to a prefilled plastic container, such as a plastic syringe, comprising an aqueous botulinum toxin formulation. The aqueous botulinum toxin formulation in the prefilled plastic container is stable for a prolonged time period. Furthermore, the present invention relates to a kit comprising the prefilled plastic container, and to the use of the prefilled plastic container for therapeutic and cosmetic purposes.

12 Claims, 1 Drawing Sheet

(56) References Cited

U.S. PATENT DOCUMENTS

| | | |
|---|---|---|
| 2009/0220545 A1 | 9/2009 | Del Giudice et al. |
| 2012/0238504 A1 | 9/2012 | Moyer et al. |
| 2013/0078295 A1 | 3/2013 | Cebrian Puche et al. |
| 2013/0211344 A1 | 8/2013 | Rodriguez et al. |
| 2013/0296779 A1 | 11/2013 | Kuehne et al. |
| 2014/0249484 A1 | 9/2014 | Jones et al. |
| 2015/0290080 A1 | 10/2015 | Weikart et al. |
| 2015/0297800 A1 | 10/2015 | Weikart et al. |
| 2016/0175408 A1 | 6/2016 | Chang et al. |
| 2016/0346480 A1 | 12/2016 | Gleason et al. |
| 2017/0100306 A1 | 4/2017 | Weikart et al. |
| 2017/0173267 A1 | 6/2017 | Ashmead et al. |
| 2017/0238580 A1 | 8/2017 | Knight et al. |
| 2017/0340823 A1 | 11/2017 | Vogt |
| 2018/0015225 A1 | 1/2018 | Vogt |
| 2018/0112246 A1 | 4/2018 | O'Keefe |
| 2019/0308007 A1 | 10/2019 | Mudd et al. |
| 2019/0374163 A1 | 12/2019 | Faarbaek et al. |
| 2020/0121855 A1 | 4/2020 | Vogt |
| 2020/0147206 A1 | 5/2020 | Jezek |

FOREIGN PATENT DOCUMENTS

| | | |
|---|---|---|
| EA | 017441 B1 | 12/2012 |
| EP | 0935970 A1 | 8/1999 |
| EP | 1997509 A1 | 12/2008 |
| EP | 2032163 A2 | 3/2009 |
| EP | 2048156 A1 | 4/2009 |
| JP | 2003-522154 A | 7/2003 |
| JP | 2012-531442 A | 12/2012 |
| JP | 2014-533177 A | 12/2014 |
| KR | 100 753 765 B1 | 8/2007 |
| KR | 10-2010-0020972 A | 2/2010 |
| WO | 00/15245 A2 | 3/2000 |
| WO | 01/58472 A2 | 8/2001 |
| WO | 2006/005910 A2 | 1/2006 |
| WO | 2006/094263 A2 | 9/2006 |
| WO | 2007/144772 A2 | 12/2007 |
| WO | 2008/145359 A1 | 12/2008 |
| WO | 2009003010 A2 | 12/2008 |
| WO | 2009/008595 A1 | 1/2009 |
| WO | 2010096134 A1 | 8/2010 |
| WO | 2010/151840 A2 | 12/2010 |
| WO | 2011/160826 A1 | 12/2011 |
| WO | 2013/071138 A1 | 5/2013 |
| WO | 2014/008138 A2 | 1/2014 |
| WO | 2014014641 A1 | 1/2014 |
| WO | 2014/026161 A1 | 2/2014 |
| WO | 2014052792 A1 | 4/2014 |
| WO | 2016036618 A1 | 3/2016 |
| WO | 2016187078 A1 | 11/2016 |
| WO | 2017220553 A1 | 12/2017 |

OTHER PUBLICATIONS

Kai Wohlfarth, et al., "Pharmacokinetic properties of different formulations of botulinum neurotoxin type A," Movement disorders: official journal of the Movement Disorder Society, (2004), vol. 19, No. S8:S65-S67.
Becton Dickinson Datasheet for 10 ml Syringe No. 300912, dated 2013 in Italian.
Becton Dickinson Datasheet for 10 ml Syringe No. 300912, dated 2017 in English.
Yixing Zhan, Encyclopedia of Methods for Manufacturing of Modern Chemical Commodity, Changsha: Hunan University Press, (1999), 262-265. Part of section 053 translated.
Yulong Zhang et al., "Formula Design and Processing Examples of Products Shaped by Plastic Compression," Beijing: National Defense Industry Press, (2006), 233-235. Part of section 4.7.4 translated.
Dressler, "Clinical Application of Botulinum Toxn," Current Opinion in Microbiology, (2021), vol. 325-336.

* cited by examiner

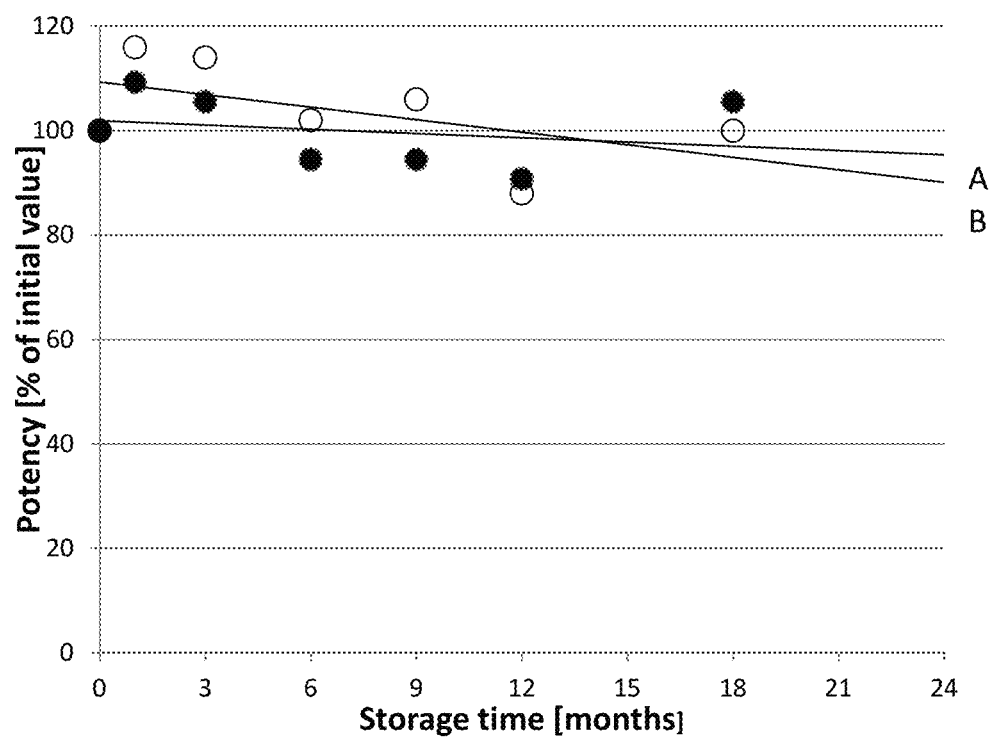

BOTULINUM TOXIN PREFILLED PLASTIC SYRINGE

CROSS-REFERENCE TO RELATED APPLICATIONS

This application is a continuation of U.S. patent application Ser. No. 16/459,382, filed on 1 Jul. 2019, which is a continuation of U.S. patent application Ser. No. 15/547,941, filed 1 Aug. 2017, now U.S. Pat. No. 10,406,290, issued 10 Sep. 2019, which is a National Stage entry of International Application No. PCT/EP2015/002600, filed Dec. 22, 2015, which claims priority to European Patent Application No. 15000310.1, filed Feb. 3, 2015. The disclosures of the priority applications are incorporated in their entirety herein by reference.

BACKGROUND

Field

The present invention relates to a prefilled plastic container, such as a prefilled plastic syringe, comprising an aqueous botulinum toxin formulation. The aqueous botulinum toxin formulation in the prefilled plastic container is stable for a prolonged time period. Furthermore, the present invention relates to a kit comprising the prefilled plastic container, and to the use of the prefilled plastic container for therapeutic and cosmetic purposes.

Description of Related Art

Botulinum toxin (BoNT) is one of the most potent toxins known and acts by blocking acetylcholine release at peripheral cholinergic neurons. BoNT is synthesized as a 150 kDa precursor neurotoxic polypeptide and is activated by selective proteolytic cleavage to yield the active two-chain BoNT form consisting of a 100 kDa heavy chain (HC; includes the translocation domain and receptor-binding domain) and a 50 kDa light chain (LC; includes the catalytic domain) linked by a disulfide bond and non-covalent interactions. There are eight homologous serotypes (A, B, $C_1$, $C_2$, D, E, F, and G) of botulinum toxin, which are produced by the bacterium *Clostridium botulinum* in the form of a complex consisting of a neurotoxic polypeptide and other (non-toxic) clostridial proteins (i.e. different hemagglutinins and a nontoxic, non-hemagglutinating protein).

Careful administration of very small doses of toxin can restrict its action locally to reduce overactive muscles and exocrine glands. Therefore, botulinum toxin is now used in the treatment of a wide range of debilitating neuromuscular diseases (e.g., cervical dystonia, blepharospasm, and spasticity), overactive exocrine glands (e.g., hyperhidrosis and hypersalivation) and other disease as well as for aesthetic purposes (e.g., treatment of facial wrinkles).

Botulinum toxins are inherently instable and, in particular, are known to be highly unstable at alkaline pH and heat-labile. Additionally, it is known that dilution of the isolated toxin complex from milligram quantities to the much lower toxin concentrations used in solutions for injection (in the nanograms per milliliter range) presents significant difficulties because of the rapid loss of specific toxicity upon such great dilution. This leads to loss of biological activity during production, reconstitution and/or storage of protein-containing pharmaceutical compositions. These problems observed with proteins may be due to chemical instability, resulting in bond formation or cleavage (e.g., hydrolysis, oxidation, racemization, β-elimination and disulfide exchange), and/or due to physical instability of the second or higher-order structure of proteins without covalent bond-breaking modification (e.g., denaturation, adsorption to surfaces, and non-covalent self-aggregation).

The stability of pharmaceutical products is, however, of paramount importance to ensure safe and efficacious use for a sufficiently long time period. Since aqueous botulinum toxin formulations are particularly prone to degradation, commercial preparations of botulinum toxin often come as vacuum-dried or lyophilized material. Examples include, for example, Botox® (onabotulinumtoxinA; Allergan, Inc.) and Dysport® (abobotulinumtoxinA; Ipsen Ltd.), which both contain the *C. botulinum* toxin complex of type A. Another example is Xeomin® (incobotulinumtoxin; Merz Pharma GmbH & Co. KGaA), which contains the pure neurotoxic component of serotype A (i.e. the 150 kDa neurotoxic polypeptide) and is devoid of any other proteins of the *Clostridium botulinum* toxin complex (i.e. the different hemagglutinins and the nontoxic, non-hemagglutinating protein).

However, while the lyophilized material has an increased stability, it has generally to be reconstituted with a pharmaceutically acceptable liquid (e.g., saline) prior to use. Lyophilized pharmaceutical products are therefore considered to be less convenient than other dosage forms. Also, the reconstitution process entails the risk of mismanagement resulting in inaccurate dosing or sterility issues. In addition, the lyophilization process is time-consuming and results in additional costs.

Another disadvantage of reconstituted solutions of botulinum toxin is that they are often not entirely used because not every patient and indication requires the same dosage. Unfortunately, due to its instability, the reconstituted toxin solution can only be stored and re-used for a relatively short period. For example, after dilution with normal saline prior to use, Botox® and Dysport® are recommended to be used within 6 hours and 4 hours, respectively. Likewise, the package leaflet of Xeomin® specifies that after storage for more than 24 hours, the reconstituted Xeomin® solution shall no longer be used.

A medical dosage form which overcomes most of these disadvantages is the prefilled syringe format, which has been become increasingly popular in recent years as drug delivery device. However, if proteins are used as active ingredients, the limited stability of proteins renders it a particularly difficult task for formulation scientists to use a prefilled syringe format. In particular, this applies to very dilute aqueous botulinum toxin solutions.

In order to increase stability of solid or liquid pharmaceutical botulinum toxin compositions, stabilizing proteins such as human serum albumin (HSA) are often added. Also, it is known to add non-proteinaceous stabilizing agents, such as surfactants, polyvinylpyrrolidone (PVP), disaccharides, polyols and the like. However, stability of liquid botulinum toxin formulations is still unsatisfactory and/or is achieved using undesirable substances for human use by injection (see, e.g., WO 01/58472, WO 2006/005910, and WO 2007/041664).

Furthermore, a liquid formulation of highly concentrated botulinum toxin type B (about 2500 U/ml) that is stable when stored in glass vials at 5° C. for up to 30 months is disclosed in WO 00/15245. However, this stability is only achieved by using vials made of glass and buffering the pH of the solution down to an acidic pH of between 5 and 6, which causes pain upon injection.

Despite the advancements in the art, there is still no injectable botulinum toxin presentation available which is not only stable over a long period to provide a sufficiently long shelf life, but is also convenient and easy to use, reduces medication errors, and minimizes the risk of contamination.

OBJECTIVE OF THE INVENTION

In view of the above, the objective of the present invention is to provide a stable medical dosage form for the administration of botulinum toxin in a convenient, safe and simple manner.

SUMMARY OF THE INVENTION

The above object is solved by the provision of a botulinum toxin prefilled plastic container (e.g., a syringe, vial, carpule or ampoule). The liquid botulinum toxin formulation in the prefilled plastic container (e.g., a syringe, vial, carpule or ampoule) is stable at 2-8° C. over a prolonged period of time to provide a sufficiently long shelf life (at least about 12-24 months).

In a first aspect, the present invention provides a prefilled plastic container (e.g., a syringe, vial, carpule or ampoule) comprising an aqueous botulinum toxin formulation, wherein the toxin activity is not reduced by more than 25%, relative to the initial toxin activity, upon storage of the prefilled container for (a) 12 months at 5° C. or (b) 3 months at 25° C.

The stability of the aqueous botulinum toxin formulation in the prefilled container (e.g., a syringe, vial, carpule or ampoule) in terms of the count (number) of sub-visible particles equal to or greater than 10 µm is also excellent and generally below 1000/ml during storage for 6 to 24 months (e.g., 6, 9, 12, 15, 18 or 24 months) at 2-25° C. (e.g., at 5° C. or 25° C.). Furthermore, the aqueous botulinum toxin formulation in the prefilled container exhibits an excellent pH stability as indicated by a pH value that is generally not increased or decreased by more than 10%, relative to the initial pH value, during storage of the prefilled container (e.g., a syringe, vial, carpule or ampoule) for 6 to 24 months (e.g., 6, 9, 12, 15, 18 or 24 months) at 2-25° C. (e.g., at 5° C. or 25° C.).

In another aspect, the present invention provides a kit comprising a prefilled plastic container (e.g., a syringe, vial, carpule or ampoule) according to the first aspect of the invention and, optionally, instructions for use of said prefilled plastic container.

In a further aspect, the present invention provides a prefilled plastic container (e.g., a syringe, vial, carpule or ampoule) according to the first aspect of the present invention for use in therapy. For example, the prefilled plastic container (e.g., a syringe, vial, carpule or ampoule) may be used for treating a disease or condition caused by or associated with hyperactive cholinergic innervation of muscles or exocrine glands in a patient including, but not limited to, dystonia, spasticity, paratonia, diskinesia, focal spasm, strabismus, tremor, tics, migraine, sialorrhea and hyperhidrosis.

In still another aspect, the present invention relates to the use of the prefilled plastic container (e.g., a syringe, vial, carpule or ampoule) according to the first aspect of the invention in cosmetic applications, such as for treating wrinkles of the skin and facial asymmetries, e.g. glabellar frown lines, crow's feet, upper facial rhytides and platysma bands.

In a yet further aspect, the present invention provides a method for the treatment of a disease or condition caused by or associated with hyperactive cholinergic innervation of muscles or exocrine glands in a patient, the method comprising locally administering an effective amount of botulinum toxin to a muscle or exocrine gland of the patient by injection using the prefilled plastic container (e.g., a syringe, vial, carpule or ampoule) according to the first aspect of the invention.

In a still further aspect, the present invention relates to a method for the cosmetic treatment of the skin, such as for treating wrinkles of the skin and facial asymmetries, the method comprising locally administering an effective amount of botulinum toxin to a patient by intradermal, subdermal or subcutaneous injection using the prefilled plastic container (e.g., a syringe, vial, carpule or ampoule) according to the first aspect of the present invention.

Further embodiments of the present invention are set forth in the appended dependent claims. The present invention may be more fully understood by reference to the following detailed description of the invention, the examples and the accompanying drawings.

BRIEF DESCRIPTION OF THE DRAWINGS

FIG. 1 shows the stability of a liquid botulinum toxin formulation in prefilled syringe configurations A (●) and B (○) at 5° C. as a function of toxin potency versus time.

DETAILED DESCRIPTION OF A PREFERRED EMBODIMENT

The present invention is based on the unexpected finding that a liquid botulinum toxin formulation in a plastic container (e.g., in the form of a syringe, vial, carpule or ampoule) shows an excellent long-term stability at reduced temperatures (e.g., 2-8° C.). Even upon storage at ambient temperature (e.g., 25° C.) the botulinum toxin prefilled container exhibits a surprisingly high stability.

Accordingly, the liquid botulinum toxin formulation prefilled container of the present invention, in particular the botulinum toxin prefilled syringe of the present invention, not only has a sufficiently long shelf life (at least about 12-24 months), but presents several additional advantages in comparison to other administration forms, such as easy and convenient use, reduced risk of medication errors, high dosing accuracy, low risk of contamination, improved sterility assurance, and high safety in administration.

Furthermore, the use of plastic materials for containers (e.g., syringes) offers advantages over glass containers (e.g., glass syringes) in terms of break resistance, decreased weight, increased flexibility for novel shapes of primary containers, improved dimensional tolerances, and absence of undesirable substances (e.g., adhesives).

Plastic materials contain various substances and additive (e.g., plasticizer) commonly referred to as leachables/extractables that are known to easily destabilize proteins, in particular if they are of a fragile nature and/or used at such low concentrations as neurotoxins (e.g., botulinum toxin). Therefore, liquid neurotoxin pharmaceutical formulations are conventionally injected using glass syringes. Surprisingly, however, the prefilled plastic container (e.g., syringe) according to the present invention was found to provide stability to an aqueous botulinum toxin formulation for a long storage time (at least about 12-24 months) at 2-8° C. and, thus, provides a sufficiently long shelf life.

As used herein, a "prefilled container" refers to any device having a partially or fully enclosed space that can be sealed or is sealed and can be used to contain, store, and/or transport liquid formulations. A "prefilled container" within the meaning of the present invention is preferably a closed (or sealed) container made of, or partially or predominantly made of, plastic (e.g., organic polymers) and includes, for example, containers in the form of (i) a syringe, (ii) a vial, (iii) a carpule, or (iv) an ampoule.

Prefilled syringes and carpules have two openings that are sealed to prevent leakage of the contents (e.g., aqueous formulations). In case of a prefilled syringe, the proximal end is sealed by a plunger stopper and the distal end is sealed by a capping device, as explained in detail herein below. In case of a plastic carpule, which is generally a plastic cylinder sterile filled with a drug formulation, the proximal end is typically sealed by a rubber stopper. This rubber stopper can be pressed in as a piston in the cylinder by the pressure of a punch of the carpule syringe. The distal end is typically sealed by a puncture membrane. The puncture membrane is pierced for injection.

A "vial" within the meaning of the present invention is a vessel, which has usually a tubular form or a bottle-like shape with a neck and is suitable for containing, storing, and/or transporting drug formulations. The single opening is sealable by different vial closure systems. For example, vials may be closed with a screw cap (screw vials), a stopper of cork, plastic or rubber (lip vials and crimp vials) and other closure systems like flip-tops or snap caps. Within the present invention a "vial" preferably means a plastic vessel having its opening sealed with a vial closure system.

In the following, the present invention is described in more detail. It is pointed out that, although the term "prefilled syringe", "prefilled plastic syringe", "syringe" or "plastic syringe" is used in the detailed description of the invention, this does not mean that it is limited to a (plastic) syringe as a particular embodiment of the (plastic) container. In fact, any reference herein to a "prefilled syringe", "prefilled plastic syringe", "syringe", "plastic syringe" or the like is to be understood as a reference to, and disclosure of, a "container" or "plastic container" and also includes, or discloses, a "vial" or "plastic vial", a "carpule" or "plastic carpule", or an "ampoule" or "plastic ampoule", unless otherwise stated.

In a first aspect, the present invention relates to a prefilled plastic syringe comprising botulinum toxin in an aqueous formulation, wherein the toxin activity is not reduced by more than 25%, relative to the initial toxin activity, upon storage of the prefilled syringe for (a) 12 months at standard refrigerator temperatures (i.e. 2-8° C., such as 5° C.), or (b) 3 months at 25° C. Preferably, the toxin activity is not reduced by more than 20%, 15%, 10% or 5%, relative to the initial toxin activity, upon storage of the prefilled syringe for 12 months at 2-8° C. (e.g., 5° C.) or is not reduced by more than 20%, relative to the initial toxin activity, upon storage of the prefilled syringe for 3 months at 25° C. Further preferably, the toxin activity is not reduced by more than 15%, 10% or 5%, relative to the initial toxin activity, upon storage of the prefilled syringe for 6 months at 2-8° C. (e.g., 5° C.).

Surprisingly, the aqueous botulinum toxin formulation in the prefilled syringe is also stable for even longer storage times of up to 24 months. For example, upon storage for up to 24 months (e.g., 15, 18 or 24 months) at 2-8° C. (e.g., 5° C.), the toxin activity is preferably not reduced by more than 30% or 25%, more preferably by no more than 20%, in particular by no more than 15%, particularly preferable by no more than 10%, and most preferable by no more than 5%, relative to the initial toxin activity.

Within the present invention, the term "toxin potency" broadly refers to a measure of drug (e.g., botulinum toxin) activity expressed in terms of the amount required to produce an effect of a given intensity. The term "activity" or "toxin activity", as used herein, refers to the biological activity of the botulinum toxin, wherein "biological activity" may refer to (a) receptor binding, (b) internalization, (c) translocation across the endosomal membrane into the cytosol, and/or (d) endoproteolytic cleavage of proteins involved in synaptic vesicle membrane fusion. For example, any light chain (LC) domain, which shows proteolytic activity of more than 10%, 20%, 30%, 40%, 50%, 60%, 70%, 80%, 90% and up to 100% of the corresponding wild-type LC domain in a SNAP-25 assay may be considered "biological active" or "to exhibit proteolytic activity" within the scope of this invention. Furthermore, any heavy chain (HC) domain that is capable of binding to a cellular HC domain receptor, in particular to its native HC domain receptor, and is capable of translocating an LC domain attached to it, is considered "biologically active".

The biological activity is commonly expressed herein in Mouse Units (MU). As used herein, 1 MU is the amount of neurotoxic component, which kills 50% of a specified mouse population after intraperitoneal injection, i.e. the mouse i.p. $LD_{50}$, as measured in accordance with the method of Schantz and Kauter (Schantz and Kauter, J. Assoc. Off. Anal. Chem. 1978, 61:96-99). The terms "MU" and "Unit" or "U" are used interchangeable herein.

Suitable assays for determining the potency or biological activity include the mouse hemidiaphragm assay (MHA) described by Pearce et al. (Toxicol. Appl. Pharmacol. 128: 69-77, 1994) and Goschel et al. (Exp. Neurol. 147:96-10, 1997), the mouse diaphragm assay (MDA) according to Dressler et al. (Mov. Disord. 20:1617-1619, 2005), a SNAP-25 protease assay (e.g., the "GFP-SNAP25 fluorescence release assay" described in WO 2006/020748 or the "improved SNAP25 endopeptidase immuno-assay" described in Jones et al., J. Immunol. Methods 329:92-101, 2008), the electrochemoluminescence (ECL) sandwich ELISA described in WO 2009/114748, and cell-based assays as those described in WO 2009/114748, WO 2004/029576, WO 2013/049508 and WO 2014/207109.

As used herein, the term "initial toxin activity" or "initial toxin potency" generally refers to the activity of the botulinum toxin at the beginning of the storage period, i.e. after manufacture of the final botulinum toxin prefilled syringe, e.g. one week or less after manufacture. Further, the term "upon storage", as used herein, is intended to mean after or at the end of storage for a given time period. In addition, the term "during storage" generally means over the course of the entire storage period.

Apart from a high stability in terms of toxin potency, the aqueous botulinum toxin formulation is also highly stable in terms of the sub-visible particle count. A "sub-visible particle" within the meaning of the present invention is typically a particle with a diameter below 100 μm. According to the present invention, the sub-visible particle count, more specifically the count (or number) of particles equal to or greater than 10 μm, in the aqueous botulinum toxin formulation is typically below 1000/ml, preferably below 600/ml and more preferably below 200/ml during storage for 6 to 24 months (e.g., 6, 9, 12, 15, 18 or 24 months) at 2-25° C. (e.g., at 5° C. or 25° C.).

Particle number measurements may be conducted by different methods, such as Micro-Flow Imaging (MFI), Resonant Mass Measurement (RMM), and Nanoparticle Tracking Analysis (NTA). The particle measurements usually follow USP <788>. Within the context of the present invention, the Micro-Flow Imaging method is preferably used. This measurement method may, for example, be conducted using a DPA-5200 particle analyzer system (ProteinSimple, Santa Clara, CA, USA) equipped with a silane coated high-resolution 100 µm flow cell. Generally, the samples are analyzed undiluted.

Alternatively, Resonant Mass Measurements (RMM) may be employed to determine the number of particles using, for example, the ARCHIMEDES Particle Metrology System (Affinity Biosensors, Santa Barbara, CA, USA) equipped with a microsensor (size range 0.3-4 µm) calibrated with 1 µm polystyrene standards. All samples are typically analyzed without dilution. The results may be analyzed using the ParticleLab software (v1.8.570) with a size bin step of 10 nm. As another alternative for determining the particle numbers, Nanoparticle Tracking Analysis (NTA) may be used, for example, using a NanoSight LM20 system (NanoSight, Amesbury, UK). The samples are typically measured undiluted. Movements of the particles in the samples may be recorded as videos for 60 seconds at ambient temperature and analyzed using suitable software (e.g., the NTA 2.3 Software).

Moreover, the aqueous botulinum toxin formulation shows high pH stability in that the pH value is essentially stable during storage of the prefilled syringe. Preferably, the pH value is not increased or decreased by more than 10%, 8% or 6%, relative to the initial pH value, upon storage of the prefilled syringe for 6 to 24 months (e.g., 6, 9, 12, 15, 18 or 24 months) at 2-25° C. (e.g., at 5° C. or 25° C.), for example for 18 months at 25° C. or for 24 months at 25° C. The pH may be measured in accordance with the US Pharmacopeia standardized test method USP <791>, which outlines pH measurements for a multitude of pharmaceutical products. Any suitable pH meter may be used, for example the Lab 870 pH meter of Schott Instruments.

As used herein, the term "prefilled syringe" refers to a syringe which is filled with a drug composition (i.e. an aqueous botulinum toxin formulation) prior to distribution to the end user who will administer the drug to the patient. The term "aqueous formulation", as used herein, is intended to refer to an aqueous solution, suspension, dispersion or emulsion, and preferably refers to an aqueous solution. Generally, a prefilled syringe includes a drug containment container forming part of a syringe body (i.e. a syringe barrel), a plunger to seal the proximal opening of the syringe and for expelling the drug, and a sealing device (e.g., a tip cap or a needle shield) on the outlet end of the syringe (e.g., the open end of the syringe tip or of a pre-mounted needle (cannula)) to seal the distal outlet opening. The term "prefilled plastic syringe" within the meaning of the present invention refers to a prefilled syringe, of which at least the barrel is made of plastic.

Within the present invention, the prefilled syringe is preferably a Luer slip or Luer lock syringe equipped with a tip cap (if no needle is pre-mounted) or a needle shield (if the needle is pre-mounted). Within the meaning of the present invention, a "luer slip syringe" is a syringe that allows a needle to be pushed on to the end of the tip, whereas a "Luer-Lock syringe" is a syringe that allows a needle to be twisted onto the tip and then locked in place. This provides a secure connection and prevents accidental removal of the needles of the injection of fluids.

The prefilled plastic syringe according to the present invention is generally sterilized (e.g., by gamma radiation, ethylene oxide (ETO) treatment and moist heat (e.g., autoclaving)). The sterilization may be carried out prior to aseptic filling with the aqueous botulinum toxin formulation or after filling with the aqueous botulinum toxin formulation. The final prefilled plastic syringe is ready-to-use. Further, the prefilled syringe described herein is usually intended for single use and intended to be disposable. Prior to sterilization, the inner surface of the plastic syringe barrel is typically coated with a lubricant to ease gliding of the plunger stopper and extruding the syringe content.

In accordance with the present invention, the aqueous botulinum toxin formulation in the prefilled plastic syringe contains the botulinum toxin at a concentration of, for example, 1 U/ml to 3000 U/ml or 10 U/ml to 1000 U/ml. Preferably, the botulinum toxin is present at a concentration of about 10 U/ml to 400 U/ml, more preferably about 25 U/ml to 200 U/ml, and most preferably about 40 U/ml to 150 U/ml (e.g., 50 U/ml, 75 U/ml or 100 U/ml).

The term "botulinum toxin", as used herein, broadly refers to any form/or type of botulinum toxin. More specifically, the botulinum toxin may be selected from botulinum toxin types A, B, C1, C2, D, E, F, G, or mixtures thereof. Preferably, the botulinum toxin is of serotype A, B or C1, particularly of serotype A.

Furthermore, the term "botulinum toxin" is intended to include both the botulinum toxin complex (the "toxin complex") and the "neurotoxic component" of a botulinum toxin (complex). As used herein, the term "botulinum toxin complex" or "toxin complex" refers to a high molecular weight complex comprising the neurotoxic component of approximately 150 kDa and, in addition, non-toxic proteins of *Clostridium botulinum*, including hemagglutinin and non-hemagglutinin proteins. The botulinum toxin serotype A complex is commercially available, for example, as Botox® (Allergan, Inc.) or as Dysport® (Ipsen, Ltd.).

The term "neurotoxic component", as used herein, relates to the neurotoxic polypeptide of the toxin complex (the "150 kDa" polypeptide; usually in its two-chain form) without any associated non-toxic proteins. The pure neurotoxic component is, for example, commercially available under the trade names Xeomin® and Bocouture® (Merz Pharmaceuticals GmbH). Preferably, the term "botulinum toxin" means the neurotoxic component of a botulinum toxin complex of a given serotype (e.g., serotype A, B or C1, particularly serotype A). In other words, the aqueous botulinum toxin formulation contained in the prefilled plastic syringe preferably contains (only) said neurotoxic component and is devoid of any other proteins of the *Clostridium botulinum* toxin complex.

It is also contemplated that the present invention encompasses functional (i.e. biologically active) isoforms, homologs, orthologs, paralogs and fragments of botulinum toxin that show at least 50%, at least 60%, at least 70%, at least 80%, at least 90% and up to 60%, up to 70%, up to 80%, up to 90%, or up to 99% sequence identity to the amino acid sequence of wild-type botulinum toxin, such as wild-type botulinum toxin A or the neurotoxic component of botulinum toxin of serotype A1 deposited with the GenBank database under the accession number AAA23262. The sequence identity can be calculated by any algorithm suitable to yield reliable results, for example by using the FASTA algorithm (W. R. Pearson & D. J. Lipman, PNAS 85:2444-2448, 1988). Sequence identity may be calculated by comparing two polypeptides or two domains such as two LC domains or fragments thereof.

Modified and recombinant botulinum toxins are also within the scope of the present invention. With respect to suitable mutants, reference is made to WO 2006/027207, WO 2009/015840, WO 2006/114308, WO 2007/104567, WO 2010/022979, WO 2011/000929 and WO 2013/068476, which are all incorporated by reference herein. Furthermore, the present invention also refers to botulinum toxins, which are chemically modified, e.g. by pegylation, glycosylation, sulfatation, phosphorylation or any other modification, in particular of one or more surface or solvent exposed amino acid(s). The modified, recombinant, isoforms, homologs, orthologs, paralogs, fragments, and mutants suitable for use within the present invention are biologically active, i.e. able to translocate into the cytosol of presynaptic cholinergic neurons and cleave proteins of the SNARE complex (e.g., VAMP/syntaxin, synaptobrevin, and SNAP-25) to exert its acetylcholine inhibitory effects.

Within the context of the present invention, the aqueous botulinum toxin formulation may comprise various other pharmaceutically acceptable substances, for example, salts (e.g., sodium chloride), stabilizing proteins (e.g., albumin, gelatin), sugars (e.g., glucose, fructose, galactose, trehalose, sucrose and maltose), carbohydrate polymers (e.g., hyaluronic acid and polyvinylpyrrolidone (PVP)), polyols (e.g., glycerol and sugar alcohols like mannitol, inositol, lactitol, isomalt, xylitol, erythritol, sorbitol), amino acids, vitamins (e.g. vitamin C), zinc, magnesium, anesthetic agents (e.g., local anesthetic agents like lidocaine), surfactants, tonicity modifiers, and the like. The term "pharmaceutically acceptable", as used herein, refers to those compounds or substances which are suitable for contact with the tissues of mammals, especially humans.

Furthermore, the term "comprise", as used herein, is intended to encompass both the open-ended term "include" and the closed term "consist (of)". The term "made of", as used herein, is intended to broadly relate to "produced of/from", in particular mainly produced from, and generally means "comprising" (indicating that other substances or materials may be included in some amounts). It may also mean "consisting of".

In accordance with the present invention, the pH of the aqueous botulinum toxin formulation in the prefilled syringe during storage is preferably in the range of 6.0 to 7.5, 6.5 to 7.5, 6.1 to 7.3 or 6.2 to 7.2, more preferably in the range of 6.3 to 7.1, and most preferably in the range of 6.5 to 7.0. A pH within the indicated range of 6.1 to 7.3 is advantageous since injections of such essentially neutral or only slightly acidic solutions are much less painful upon injection than acidic solutions with a pH of below 6.

The term "aqueous formulation" or "aqueous botulinum toxin formulation", as used herein, is not particularly limited and may refer to an aqueous suspension, aqueous dispersion, aqueous emulsion and is preferably an aqueous solution.

Preferably, the aqueous botulinum toxin formulation preferably does not contain a buffer like a phosphate buffer, a phosphate-citrate buffer, a lactate buffer, an acetate buffer and the like. The term "buffer" as used herein denotes a pharmaceutically acceptable excipient, which stabilizes the pH of a pharmaceutical preparation. Furthermore, the aqueous botulinum toxin formulation may be free of amino acids (e.g., methionine) and/or surfactants (e.g., polysorbates such as polysorbate 80) and/or animal-derived proteins (e.g., human serum albumin (HSA) or bovine serum albumin (BSA)).

A preferred aqueous botulinum toxin formulation for use herein comprises water, botulinum toxin (e.g., the neurotoxic component of botulinum toxin, preferably of serotype A) at a concentration of, e.g., 10 to 150 U/ml, a salt (e.g., sodium chloride) in a concentration of, e.g., 0.5% to 1.5% w/v, a sugar (e.g., a mono- or disaccharide, such as glucose, fructose, galactose, trehalose, sucrose and maltose) at a concentration of, e.g., 0.1% to 2% w/v, and a stabilizing protein (e.g., albumin) at a concentration of, less than 4%, 3%, 2% or 1% w/v, e.g., 0.01% to 1% w/v.

A particularly preferred aqueous botulinum formulation for use herein essentially consists of water, botulinum toxin (e.g., the neurotoxic component of botulinum toxin type A), sodium chloride, sucrose, and albumin (e.g., human serum albumin; HSA). The concentration of the mentioned ingredients may be in the following ranges: 10 to 200 U/ml, preferably 30 to 125 U/ml (botulinum toxin); 0.5% to 1.5% w/v, preferably 0.7% to 1.1% w/v (sodium chloride); 0.1% to 2% w/v, preferably 0.2% to 1% w/v (sucrose); 0.01% to 1% w/v, preferably 0.05% to 0.5% w/v (HSA). Another particularly preferred botulinum toxin formulation for use herein is a Xeomin® solution, e.g., a Xeomin® solution reconstituted with physiological saline (0.9% sodium chloride), containing 20 to 150 U/ml of the neurotoxic component of botulinum toxin type A.

The term "essentially consists of", as used herein is intended to mean that substances other than those indicated are only contained in trace amounts, e.g. unavoidable impurities contained in the components used for formulating the aqueous botulinum toxin formulation or impurities included in the isolated botulinum toxin (e.g., the neurotoxic component of botulinum toxin type A) in very low amounts as a result of the purification procedure (e.g., very low residual amounts of buffers, chelating agents and the like).

In accordance with the present invention, the configuration of the prefilled plastic syringe is not particularly limited and generally comprises a fluid-receiving barrel that, after filling, is removably capped by a capping device to sealingly close the distal end of the syringe (e.g., by a "tip cap" that is removed and replaced by a needle prior to use, or a sealing means like a needle shield in case of a prefilled syringe with a removable or permanent needle), and is closed at the proximal end by its plunger or any other means that is in fluid-tight engagement with the inner wall of the barrel. To use the prefilled syringe, the tip cap, needle shield or other type of capping device is removed, optionally a needle is attached (if not already present), and the plunger tip or piston is advanced in the barrel to inject the contents (i.e. the aqueous botulinum toxin formulation) of the barrel into a patient.

The prefilled plastic syringe according to the present invention preferably comprises:
  (a) a plastic syringe barrel including a proximal end and a distal end, and a generally cylindrical wall extending therebetween and defining a barrel lumen, the syringe barrel having a distally projecting tip with a fluid passage extending therethrough and communicating with the barrel lumen, wherein the generally cylindrical wall has an interior surface optionally coated with a barrier layer,
  (b) a capping device having an outlet engaging portion sealingly engaging and closing the distal open outlet end of the syringe, wherein the outlet engaging portion is made of an elastomeric material that optionally has a coating on its surface, and
  (c) a plunger rod assembly which extends into the proximal end of the syringe barrel and includes a plunger stopper in sliding fluid-tight engagement with the cylindrical wall of the barrel lumen, wherein the plunger stopper is made of an elastomeric material, which optionally has a coating on at least a portion of the plunger stopper contacting the aqueous botulinum toxin formulation during storage and/or injection.

The materials of the prefilled syringe that have the potential to interact with the aqueous botulinum toxin formulation in the prefilled syringe are generally selected to minimize or limit the amount of extractables and leachables since extractables/leachables have the potential to contaminate the aqueous botulinum toxin formulation and to impair the stability, e.g., in terms of biological activity or potency, of the botulinum toxin.

As used herein, the terms "extractable(s)" and "leachable(s)" refer to chemical species that can be released from a container or component of material of the prefilled plastic syringe and/or has migrated from syringe materials into the aqueous botulinum toxin formulation under normal conditions of use or storage. Methods for identification of extractables/leachables are known in the art and based on recommended industry practices and International Conference for Harmonisation (ICH) guidelines (see, e.g., FDA guidance, Container Closure Systems for Packaging Human Drugs and Biologics). Exemplary methods include, e.g., Liquid Chromatography/Mass Spectrophotometry (LC/MS), Gas Chromatography Spectroscopy/Mass Spectrophotometry (GC/MS), Inductively Coupled Plasma (ICP) and Infrared (IR).

Within the context of the present invention, the inside surface of the plastic barrel may be coated or may not be coated. It is, however, usually coated with a barrier layer for lubrication purposes (in the following also referred to as "lubricant layer"). The lubricant layer should not only provide high lubricity, enabling the plunger to easily glide through the barrel, but also be compatible with the aqueous botulinum toxin formulation and protect its shelf life. Within the context of the present invention, the lubricant layer may be a silicone-free lubricant layer or a silicone lubricant layer.

Likewise, the inner surface of the plastic vessel part of the vial, the inner surface of the plastic cylinder of the carpule, and the inner surface of the plastic ampoule may be optionally coated with a barrier layer and, in particular, with a silicone-free layer or a silicone layer. Thus, all comments provided below with regard to the silicone-free lubricant layer and the silicone lubricant layer of the plastic syringe equally apply to the silicone-free layer and silicone layer, respectively, of the plastic vial, plastic carpule and plastic ampoule.

Suitable silicone-free fluoropolymer lubrication layers may be made of the materials described below for the optionally present coatings of the capping device (or more specifically of the outlet engaging portion) and the plunger stopper. Preferred silicone-free lubrication layers include fluoropolymer (fluorocarbon) layers, in particular ethylenetetrafluoroethylene (ETFE) layers and perfluoropolyether-based (PFPE-based) layers (e.g., TriboGlide®), as well as silicon oxide-based glass PECVD (plasma-enhanced chemical vapor deposition) coatings.

Such fluoropolymer layers can be prepared as known in the art, for example by spraying plastic syringe barrels with a perfluoropolyether oil to achieve a thin layer of lubricant on the inside surface of the syringe, followed by exposing the inner cavities to a downstream inert gas (e.g., argon or helium) plasma. The plasma treatment leads to crosslinking of the perfluoropolyether, thereby immobilizing the coating and reducing its tendency to migrate off the target surface, resulting in less particles that potentially impairs the stability/efficacy of the botulinum toxin drug. An exemplary production process is described in WO 2014/014641 A1, the content of which is incorporated herein by reference. Furthermore, a particularly suitable silicone-free barrier coating for use herein is known in the art as TriboGlide® coating, a perfluoropolyether coating crosslinked by plasma treatment.

A suitable silicone lubricant layer for use herein may be prepared by a siliconization method selected from, but not limited to, silicone oil-based methods (e.g., spray-on siliconization or baked-on siliconization) and vapor deposition methods (e.g., plasma enhanced chemical vapor deposition (PECVD)). Preferably, the silicone lubricant layer is formed by spray-on siliconization or, more preferably, by baked-on siliconization.

In the spray-on siliconization method, a silicone oil (e.g. DOW CORNING® 360 with a viscosity of 1000 cSt) is sprayed into the syringe (i.e. the barrel) using, e.g., a diving or static nozzle to produce a thin silicone oil layer. While silicone oil is an excellent lubricant, excess silicone oil can lead to the formation of unwanted visual and subvisual silicone oil particles. With protein-based drugs, in particular, these silicone oil particles may lead to undesirable interactions with protein drugs. For example, subvisual silicone oil particles are thought to promote protein aggregation. Therefore, since it results in fewer sub-visual and visual silicone oil particles, the baked-on siliconization processes is particularly preferred for use herein. It involves the application of silicone oil as an emulsion (e.g., DOW CORNING® 365 siliconization emulsion), which is then baked on the plastic surface at a specific temperature and for a specific time.

The design of the syringe plastic barrel is not particularly limited and typically has an inside diameter adjusted to accommodate the desired fill volume of, e.g., 0.5 cm3, 1.0 cm3, 1.5 cm3 or 2.0 cm3. Usually, the syringe barrel has graduated marks indicating the volume of fluid in the syringe. In addition, the syringe barrel may include a flange-style interface. The design of the flange may, for example, be compatible with ISO11040. The flange-style interface may further be compatible with an optionally present handle.

The syringe tip is usually integrally formed (e.g., molded) with the syringe plastic barrel. Preferably, the syringe barrel includes an integrally formed Luer lock tip or an integrally formed Luer slip tip. The tip is formed with an integral passage extending axially through the tip and being in communication with the chamber for dispensing the contents of the syringe barrel. The tip may have a substantially frustoconical shape that converges from the distal outlet end of the syringe barrel towards the tip's outlet end. Alternatively, the tip may be characterized as divergent (i.e., expanding from a smaller diameter to a larger one). Furthermore, the tip is usually located centrally in relation to the body of the syringe (concentric syringe tip) but may also be located offset towards the edge of the body (eccentric syringe tip).

With respect to the material of the syringe plastic barrel, the plastic material is preferably a cycloolefin polymer (COP), a cycloolefin copolymer (COC) or a mixture thereof. COCs are produced by polymerization of cyclic monomers such as norbornene with ethane while COPs are produced by ring-opening metathesis of cyclic monomers followed by hydrogenation. The COC, COC and COP/COC materials exhibit a number of desirable characteristics, including high transparency, low density, excellent moisture barrier capabilities, and resistance to aqueous and polar organic media. Specific examples include Topas® COC and Daikyo Crystal Zenith®.

The plastic vials, carpules and ampoules may be made of the plastic materials described above in relation to the plastic syringe barrel, polyethylene (PP, e.g., HDPE, LDPE), polyester, polyethylene terephthalate (PET), polyamides, and mixtures thereof. It is also contemplated that the plastic vials, carpules and ampoules have a multilayered structure with on layer being made of one of the said materials and the other layer(s) made of one (or more) other materials.

In accordance with the present invention, the "capping device" broadly refers to any means for closing and sealing the distal open outlet end of a syringe. Within the present invention, the term "open outlet end" or "distal open outlet end" refers to any distal open end of a syringe that is in fluid communication with the barrel lumen. The capping device generally has a channel with a closed end and an open end having a dimension for receiving and efficiently sealing the open outlet end of the syringe to prevent leakage.

In case of a prefilled plastic syringe without pre-mounted needle, the capping device is a capping means commonly known as "tip cap". The tip cap forms a fluid-tight seal with the tip of the syringe to efficiently close the syringe barrel and to prevent leakage of the contents of the syringe barrel. The tip cap is usually removable coupled to the syringe tip or a luer collar. The luer collar surrounds the top of the syringe barrel (e.g., syringe tip). Preferably, the luer collar has internal threads and the tip cap has external threads complementing said internal threads of said luer collar for coupling the tip cap to the syringe barrel. In case of the prefilled plastic syringe of the present invention, the luer collar is generally integrally formed (e.g., unitarily molded with) the syringe barrel. Prior to use, the tip can be removed, and a needle cannula (needle assembly) can then be securely coupled to the syringe tip.

In case the prefilled plastic syringe includes a removable or non-removable (i.e. permanent) cannula or needle cannula (also referred to as "needle" or "needle assembly") extending from the syringe tip for delivering the aqueous botulinum toxin formulation from said syringe, the capping device may be referred to as "needle shield". Said needle shield generally has a channel with a closed end and an open end having a dimension for receiving and coupling with the cannula (needle) mounted on the tip of the syringe. Typically, the (sharpened) end of the cannula penetrates the closed end of the channel in the needle shield to seal the open end of the cannula.

The capping device (e.g., tip cap or needle shield) may be a unitary member and usually made from a flexible and resilient polymeric material (e.g., an elastomer), or can have an outer cap made of a rigid plastic material that is coupled to a flexible and resilient inner cap or material comprising, or made of, e.g., an elastomer, at least a portion of which contacts and seals the distal opening of the syringe. Generally, at least an outlet engaging portion that contacts the distal tip opening to form a fluid-tight seal is made from a flexible and/or resilient material (e.g., an elastomer) and, since the engaging portion contacts the aqueous botulinum toxin formulation during storage and/or use, is preferably made of a material having a minimized potential for unwanted extractables/leachables. In order to further decrease the amount of extractables and/or leachables and to increase compatibility with the aqueous botulinum toxin formulation, the outlet engaging portion may have a coating thereon.

Suitable flexible and/or resilient materials of the capping device, in particular of the outlet engaging portion, include elastomers that do not interfere with the aqueous botulinum toxin formulation and enable long-term storage. In particular, the part of the sealing device that contacts, or is configured to contact, the aqueous botulinum toxin formulation (i.e. the outlet engaging portion) should exhibit low extractable/leachable levels during prolonged storage of the aqueous botulinum toxin formulation. As used herein, the term "elastomer" or "elastomeric material" refers primarily to crosslinked thermosetting rubbery polymers that are more easily deformable than plastics but that are approved for use with pharmaceutical grade fluids and are not readily susceptible to leaching or gas migration.

Preferably, the elastomeric material suitable for use herein is selected from isoprene rubber (IS), butadiene rubber (polybutadiene, BR), butyl rubber (copolymer of isobutylene and isoprene; IIR), halogenated butyl rubber (e.g., chloro butyl rubber, CIIR; and bromo butyl rubber: BIIR), styrene-butadiene rubber (copolymer of styrene and butadiene, SBR), and mixtures thereof. Preferably, the elastomeric material is butyl rubber or a halogenated butyl rubber, particularly a bromo butyl rubber or a chloro butyl rubber, or a mixture thereof. The elastomeric material may also be reinforced with an inert mineral. Further, it may be cured (e.g., with organic peroxide, phenolic resins, etc.).

Suitable coatings that may be optionally present on the outlet engaging portion made from, e.g., the above-mentioned elastomeric materials, are generally made of a material that does not undesirably interfere with the aqueous botulinum toxin formulation and exhibits low levels of extractables/leachables. Coatings for use herein include, but are not limited to, polypropylene, polyethylene, parylene (e.g., parylene N, parylene C and parylene HT), crosslinked silicone and, preferably, fluoropolymer coatings. Examples of suitable crosslinked silicone coatings include the B2-coating (Daikyo Seiko) or XSi™ (Becton Dickinson).

The fluoropolymer coatings include, but are not limited to, fluorinated ethylene-propylene copolymers (e.g., tetrafluoroethylene-hexafluoropropylene copolymer (FEP)), fluorinated ethylene-ethylene copolymers (e.g., ethylene tetrafluoroethylene copolymer (ETFE), such as FluroTec®), PVA (a copolymer of tetrafluoroethylene (TFE) and perfluoropropylvinylether (PPVE)), tetrafluoroethylene-perfluoroethylene copolymers, polyvinylidene fluoride (PVDF), polyvinyl fluoride (PVF), polytetrafluoroethylene (PTFE), and mixtures thereof. Preferably, the coating is made of ETFE and, particulary, is a FluroTec® coating.

With regard to the carpule of the present invention, the distal end is sealed by a puncture membrane. The puncture membrane may be formed from a thin rubber or silicone, a thin plastic/polymer, a film such as Mylar, a polyolef in such as polyethylene or polypropylene, a metal foil such an aluminum foil, etc. The membrane may be between about 0.001 and 2.0 mm, usually between 0.002 mm and 0.65 mm thick. Also, the membrane may be made of an elastomeric material and optionally have a coating as described above in connection with the capping device of the prefilled plastic syringe.

With regard to the vial of the present invention, the vial closure system (e.g., cap), in particular those portions of the vial closure system that come into contact with, or have the potential to come into contact with and/or seal the vial (e.g., a septum) may be made of an elastomeric material, in particular a thermoplastic elastomeric material, more particularly a styrenic block copolymer thermoplastic elastomer, or of an elastomeric material as described above in connection with the capping device of the prefilled plastic syringe of the present invention. Another suitable material is a silicone material. Furthermore, the said materials may have an optional coating, in particular a fluoropolymer coating, as defined above in relation to the capping device of the prefilled plastic syringe.

In accordance with the present invention, the prefilled syringe generally includes a plunger rod assembly, which extends into the proximal end of the syringe barrel. The plunger rod assembly may include a rod (also known as pushrod) with a plunger stopper at its tip (also known as "plunger") in sliding fluid-tight engagement with the cylindrical wall of the barrel lumen. The plunger forms the proximal seal and the dynamic seal that allows for extrusion of the liquid botulinum toxin formulation. The plunger stopper contacts the aqueous botulinum toxin formulation during storage and/or administration. Therefore, the plunger stopper should be compatible with the aqueous botulinum toxin formulation and not impair its long-term stability. In particular, the plunger stopper should preferably be designed to minimize the amount of extractables/leachables upon long-time storage.

Within the present invention, the plunger stopper is preferably made of an elastomeric material, which optionally has a coating on at least a portion of the plunger stopper that contacts, or is capable of contacting, the aqueous botulinum toxin formulation during storage and/or use. Suitable plunger stopper elastomeric materials for use herein include, but are not limited to, isoprene rubber (IS), butadiene rubber (polybutadiene, BR), butyl rubber (copolymer of isobutylene and isoprene, IIR), halogenated butyl rubber (e.g., chloro butyl rubber, CIIR; and bromo butyl rubber, BIIR), styrene-butadiene rubber (copolymer of styrene and butadiene, SBR), and mixtures thereof. Preferably, the plunger stopper material is a butyl rubber or a halogenated butyl rubber or a mixture thereof, particularly a bromo butyl rubber or a chloro butyl rubber. The elastomeric material may also be reinforced with an inert mineral. Further, it may be cured (e.g., with organic peroxide, phenolic resins, etc.).

Preferably, the plunger stopper comprises a coating acting as a barrier film. The coating is usually applied to at least the seal surfaces, including the surface portion of the plunger stopper facing the barrel lumen and contacting the aqueous botulinum toxin formulation during storage and/or use. The coating serves the purpose of providing good lubricity while minimizing interaction between the plunger stopper and the liquid botulinum toxin formulation.

Suitable coatings of the plunger stopper are generally made of a material that does not undesirably interfere with the aqueous botulinum toxin formulation and exhibits low levels of extractables/leachables. Such coatings include, but are not limited to, polypropylene, polyethylene, parylene (e.g., parylene N, parylene C and parylene HT), crosslinked silicone and, preferably, fluoropolymer coatings. Examples of suitable crosslinked silicone coatings include the B2-coating (Daikyo Seiko) or XSi™ (Becton Dickinson).

The fluoropolymer coatings include, but are not limited to, fluorinated ethylene-propylene copolymers (e.g., tetrafluoroethylene-hexafluoropropylene copolymer (FEP)), fluorinated ethylene-ethylene copolymers (e.g., ethylene tetrafluoroethylene copolymer (ETFE), such as FluroTec®), PVA (a copolymer of tetrafluoroethylene (TFE) and perfluoropropylvinylether (PPVE)), tetrafluoroethylene-perfluoroethylene copolymers, polyvinylidene fluoride (PVDF), polyvinyl fluoride (PVF), polytetrafluoroethylene (PTFE), and mixtures thereof. Preferably, the coating is made of ETFE and, particulary, is a FluroTec® coating.

The design of the plunger stopper is not particularly limited and may be a nested or bagged stopper. Further, the interface to the rod may be threaded to allow installation of the rod after sterilization. Alternatively, the interface to the rod may be designed with a snap-on design. The rod, like the plunger stopper, is generally designed to withstand sterilization but is not otherwise limited in any particular way. Typically, the rod is made of a plastic material such as an ethylene vinyl acetate (EVA) copolymer or polypropylene.

The rubber stopper of the carpule of the present invention may comprise, or be made of, the same elastomeric materials as described above in connection with the plunger stopper of the plastic syringe. Also, the rubber stopper of the carpule may have the same optional coating as defined above with respect to the coating on the plunger stopper. Further, the coating may be on at least a portion of the rubber stopper that contacts the aqueous botulinum toxin formulation during storage and/or use.

Within the framework of the present invention, the prefilled plastic syringe including the capping device, the syringe barrel, and the plunger assembly before and after sterilization (e.g., by gamma radiation, ethylene oxide or autoclaving) meet or exceed the standards for extractable substances as determined by The Japanese Pharmacopoeia, 14th Edition, No. 61, *Test Methods for Plastic Containers* (2001) as well as the standards of The Japanese Pharmacopoeia, 14th Edition, No. 59, *Test for Rubber Closure for Aqueous Infusions*. Furthermore, the polymer composition of the capping device and plunger stopper after sterilization satisfies the combustion tests of No. 61 of The Japanese Pharmacopoeia, *Test Methods for Plastic Containers* (2001), as well as the acceptable limits for extractable substances as defined by the foaming test, pH test, potassium permanganate-reducing substances test, UV spectrum test and residue on evaporation test according to The Japanese Pharmacopoeia, No. 61, *Test Methods for Plastic Containers* (2001).

In another aspect, the present invention relates to a kit comprising a prefilled plastic container (e.g., a syringe, vial, carpule or ampoule) according to the present invention and, optionally, instructions for use of said prefilled plastic container.

In a further aspect, the present invention relates to a prefilled plastic container (e.g., a syringe, vial, carpule or ampoule) according to the present invention for use in therapy. In particular, the prefilled plastic container according to the present invention may be used in the treatment of a disease or condition caused by or associated with hyperactive cholinergic innervation of muscles or exocrine glands in a patient.

Within the context of the present invention, if the container is not a syringe (e.g., a vial, carpule or ampoule), the content of these "non-syringe type" containers (i.e. the aqueous botulinum toxin formulation) is generally injected to the desired target site using a suitable injection device (e.g., a syringe) in the same manner as described herein in relation to the prefilled plastic syringe. The carpules are inserted into a carpule injection device as known to those skilled in the art. The contents of the vials and ampoules are generally aseptically filled into a syringe and then injected to the target site using a suitable injection device (e.g., a syringe) in the same manner as described herein in relation to the prefilled plastic syringe.

The term "hyperactive cholinergic innervation", as used herein, relates to a synapse, which is characterized by an unusually high amount of acetylcholine release into the synaptic cleft. "Unusually high" relates to an increase of, e.g., up to 25%, up to 50% or more with respect to a reference activity which may be obtained, for example, by comparing the release with the release at a synapse of the same type but which is not in a hyperactive state, wherein muscle dystonia may be indicative of the hyperactive state. "Up to 25%" means, for example, about 1% to about 25%. Methods for performing the required measurements are known in the art.

Within the present invention, the disease or condition caused by or associated with hyperactive cholinergic innervation of muscles includes, but is not limited to, dystonias (e.g., blepharospasm, spasmodic torticollis, limb dystonia, and task-specifc dystonias such as writer's cramps), spasticities (e.g., post-stroke spasticity, spasticity caused by cerebral palsy), paratonia, diskinesias (e.g., tardive diskinesia), focal spasms (e.g., hemifacial spasm), (juvenile) cerebral palsy (e.g., spastic, dyskinetic or ataxic cerebral palsy), strabismus, pain (e.g. neuropathic pain), wound healing, tremors, tics, and migraine.

The prefilled botulinum toxin container (e.g., a syringe, vial, carpule or ampoule) of the present invention is particularly useful in the treatment of dystonia of a muscle. Exemplary dystonias include, but are not limited to, dystonias selected from the group consisting of (1) cranial dystonia, including blepharospasm and oromandibular dystonia of the jaw opening or jaw closing type, (2) cervical dystonia, including antecollis, retrocollis, laterocollis and torticollis, (3) pharyngeal dystonia, (4) laryngeal dystonia, including spasmodic dysphonia, (5) limb dystonia, including arm dystonia such as task specific dystonias (e.g., writer's cramp), leg dystonia, axial dystonia, segmental dystonia, and (6) other dystonias.

The term "hyperactive exocrine gland", as used herein, is not particularly limited and covers any exocrine gland with hyperactivity. It is therefore envisaged that the present invention can be applied to the treatment involving any of the glands mentioned in Sobotta, Johannes, Atlas der Anatomie des Menschen, 22. Auflage, Band 1 and 2, Urban & Fischer, 2005, which is incorporated herein by reference. Preferably, the hyperactive gland is an autonomic exocrine gland. The botulinum toxin composition is preferably injected into or in the vicinity of the hyperactive exocrine gland.

Within the present invention, the hyperactive exocrine glands include, but are not limited to, sweat gland, tear gland, salivary gland, and mucosal gland. Furthermore, the hyperactive gland may also be may be associated with a disease or condition selected from the group consisting of Frey syndrome, Crocodile tears syndrome, axillar hyperhidrosis, palmar hyperhidrosis, plantar hyperhidrosis, hyperhidrosis of the head and neck, hyperhidrosis of the body, rhinorrhea, or relative hypersalivation in patients with stroke, Parkinson's disease or amyotrophic lateral sclerosis. In particular, the disease or condition caused by or associated with hyperactive cholinergic innervation of exocrine glands may include drooling (hypersalivation, sialorrhea) and excessive sweating (hyperhidrosis).

The administration is not limited to any particular administration regimen, mode, form, dose and interval. As known to those skilled in the art, the administered amount or dose of botulinum toxin depends on the mode of application, the type of disease, the patient's weight, age, sex and state of health, and which target tissues are chosen for injection. The botulinum toxin formulation is usually administered locally, e.g., by subcutaneous or intramuscular injection into or in the vicinity of the target tissues (e.g., muscles, skin, exocrine glands).

Different muscles, depending on their size, generally require different dosing. A suitable dose may range from 10 to 2000 U, preferably from 50 to 500 U, and more preferably from 100 to 350 U of botulinum toxin. For the treatment of exocrine glands, the dose is usually in the range of 10 to 500 U, preferably 20 to 200 U, and more preferably 30 to 100 U. Such total amounts may be administered on the same day or on a subsequent day of treatment. For example, during a first treatment session a first fraction of the dose may be administered. During one or more treatment sessions, the remaining fraction of the total dose may be administered. Further, the frequency of application is not particularly limited and suitable administration intervals may be three months or less (e.g., 4 or 8 weeks) or more than three months.

In still another aspect, the present invention relates to the use of the prefilled plastic container (e.g., a syringe, vial, carpule or ampoule) according to the present invention in cosmetic applications, such as for treating facial asymmetries and wrinkles/lines of the skin (e.g., facial lines and facial wrinkles), including upper facial rhytides, platysma bands, glabellar frown lines, horizontal forehead lines, nasolabial folds, chin folds, popply chin, mental ceases, marionette lines, buccal commissures, perioral wrinkles, crow's feet, and jawlines. Preferably, the prefilled botulinum toxin container (e.g., a syringe, vial, carpule or ampoule) of the present invention is used for injection into glabellar frown lines, crow's feet, perioral wrinkles, and/or platysma bands.

The amounts of botulinum toxin administered for cosmetic application are usually in the range of 1 to 5 U, 5 to 10 U, 10 to 20 U or 20 to 50 U. Such total amounts may be administered on the same day or on a subsequent day of treatment. For example, during a first treatment session a first fraction of the dose may be administered. This first fraction is preferably a suboptimal fraction, i.e. a fraction, which does not remove the wrinkles or skin lines completely. During one or more treatment sessions, the remaining fraction of the total dose may be administered. Regarding further details of administration, it is referred to the disclosure provided above in relation to the therapeutic use.

In a yet further aspect, the present invention relates to a method of treating a disease or condition caused by or associated with hyperactive cholinergic innervation of muscles or exocrine glands in a patient, the method comprising locally administering an effective amount of botulinum toxin to a muscle or exocrine gland of the patient using the prefilled plastic container (e.g., a syringe, vial, carpule or ampoule) according to the present invention.

As used herein, the term "effective amount" refers to the amount of a botulinum toxin sufficient to effect beneficial or desired therapeutic, cosmetic or anesthetic results. The term "patient", as used herein, generally relates to a human afflicted with a disease or condition caused by or associated with hyperactive cholinergic innervation of muscles or exocrine glands, or to a human in need of a cosmetic or anesthetic treatment. As used herein, "patient" may be interchangeably used with "subject" or "individual".

The term "local administration" within the meaning of the present invention refers preferably to subcutaneous or intramuscular injection into or in the vicinity of the target tissues (e.g., muscles, skin, exocrine glands). With respect to the administration (e.g., regimen, mode, form, dose and interval) and the disease or conditions to be treated, the same comments apply as those set out above in relation to the use of the glass container (e.g., the prefilled botulinum toxin syringe) for cosmetic and therapeutic applications.

In a still further aspect, the present invention relates to a method for the cosmetic treatment of the skin, such as for treating wrinkles of the skin and facial asymmetries, the method comprising locally administering an effective amount of botulinum toxin to a patient by intradermal, subdermal or subcutaneous injection using the prefilled plastic container (e.g., a syringe, vial, carpule or ampoule) according to the present invention.

Exemplary cosmetic applications include those mentioned above. With regard to the meaning or definition of the terms "effective amount", "patient", the administration (e.g., regimen, mode, form, dose and interval), and the disease or conditions to be treated, the comments provided above with regard to other aspects of the present invention similarly apply, unless otherwise stated.

The present invention will now be further illustrated by the following, non-limiting examples.

EXAMPLES

The following examples show that, contrary to expectation and common belief in the art, an aqueous botulinum toxin formulation stored in a prefilled syringe system exhibits an excellent stability for a prolonged time period (e.g., for 9-12 months) at standard refrigerator temperature (2-8° C.). Furthermore, extrapolation of the measured stability data indicates that the prefilled botulinum toxin syringe is highly stable for at least 12 to 24 months at 2-8° C.

Accordingly, the botulinum toxin's presentation can be changed from a lyophilized vial to a prefilled plastic syringe format, which meets the demands of physicians and patients looking for easier, safer and more accurate modes of administration.

Materials & Methods

An aqueous botulinum liquid botulinum toxin formulation was prepared by dissolving 1.0 mg human serum albumin (HSA), 4.7 mg sucrose, and incobotulinum-toxinA in 0.9% saline to a concentration of 50 U/ml. The formulation was then filled into a syringe plastic barrel with a Luer-Lock-type closure comprising a Luer-Lock and a tip cap which, when fitted, contacts the opening of the distal syringe tip in order to seal the syringe barrel. Afterwards, a plunger stopper was inserted into the proximal end portion of the barrel in order to close the proximal opening. The resulting prefilled plastic syringe was then stored at a temperatures of 5° C. or 25° C. Then, the stability of the aqueous botulinum toxin formulation at t=0, 1, 3, 6, 9 and 12 months was assessed by determining the remaining toxin potency, pH value, and sub-visible particle count.

The toxin potency was determined using a mouse hemi-diaphragm assay (HDA) according to Goschel et al. (Exp. Neurol. 147:96-102, 1997). In brief, the assay was conducted by maintaining a murine nerve muscle preparation in an organ bath containing 4 ml of medium. The muscle was attached to a force transducer and electrically stimulated via the phrenic nerve resulting in an isometric contraction force which remained constant for more than 180 min if no toxin was added. Upon introduction of toxin to the organ bath, the contraction amplitude of the nerve-stimulated muscle gradually declines. The contraction amplitude of the diaphragm was monitored over time. As a read-out, the time at which half the initial contraction force is reached was determined and referred to as "paralysis time". Increased time values, compared to initial values, reflect lower amounts of active toxin and loss of toxin potency, respectively.

The pH measurements were performed in accordance with the US Pharmacopeia standardized test method USP <791>, which outlines pH measurements for a multitude of pharmaceutical products, using a pH meter (Lab 870, Schott Instruments).

Particle measurements were conducted using Micro-Flow Imaging (MFI) by means of a DPA-5200 particle analyzer system (ProteinSimple, Santa Clara, CA, USA) equipped with a silane coated high-resolution 100 μm flow cell. The samples were analyzed undiluted. MFI View System Software (MVSS) version 2-R2-6.1.20.1915 was used to perform the measurements, and MFI View Analysis Suite (MVAS) software version 1.3.0.1007 was used to analyze the samples.

Two different prefilled plastic syringe systems (in the following "configurations A and B"), which differ from each other by the plunger stopper, were studied. Details of the syringe configurations examined are summarized in Table 1.

TABLE 1

| | | Syringe configurations A and B | | | | | |
|---|---|---|---|---|---|---|---|
| | | SYRINGE BARREL | | TIP CAP | | PLUNGER STOPPER | |
| CONF. | COMP. | Product Name | Material | Product Name | Material | Product Name | Material |
| A | GH[1] | ClearJect 1 ml long LL2 T4 (Taisei Kako) | Cyclo-olefin polymer(COP); barrel is siliconized[2,3] | Tip Cap 4 (Sumitomo) | Sumitomo P-134 (chlorinated butyl rubber)[3] | 1 mL Pi1 (Sumitomo) | Sumitomo P-134 (chlorinated butyl rubber; coated with cross-linked silicone)[3] |
| B | GH[1] | See configuration A | See configuration A | See configuration A | See configuration A | West ® 4023/50 G NovaPure ® | Elastomer formulation (bromobutyl reinforced with inert mineral) coated with FluroTec ® film |

[1] = Gerresheimer

[2] = siliconized with Dow Corning Medical Fluid 360 (viscosity 12,500 cSt)

[3] = sterilized by gamma-irradiation in accordance with ISO 11137

Results

The results of the stability measurements in terms of remaining toxin potency for configurations A and B are shown in Table 2 below.

TABLE 2

Stability in terms of potency

STABILITY (toxin potency in %, relative to initial toxin activity)

| | | | Time (months) | | | | | |
|---|---|---|---|---|---|---|---|---|
| CONFIG. | Temperature | t = 0 (initial)* | 1 | 3 | 6 | 9 | 12 | 18 |
| A | 2-8° C. | 100 | 109 | 106 | 94 | 94 | 91 | 106 |
| B | | 100 | 116 | 114 | 102 | 106 | 88 | 100 |
| A | 25° C. | 100 | 94 | 85 | 65 | 0 | n.d.** | n.d. |
| B | | 100 | 116 | 78 | 54 | 0 | n.d. | n.d. |

*initial absolute toxin activity in units ranged from 50 U to 54 U
**n.d. = not determined As is evident from Table 2, the toxin essentially maintains its initial potency at 2-8° C. over time, i.e. there is essentially no potency loss after storage for no less than 18 months (a potency loss of <10% after storage for 18 months). Even at room temperature (i.e., 25° C.), the stability is still acceptable, as indicated by a potency loss of no more than about 20% after 3 months.

An extrapolation of the stability data for configurations A and B at 2-8° C. up to a storage time of 24 months is graphically shown in FIG. 1. As can be seen, the estimated maximum loss of biological activity after 24 months is expected to be about 10% and, thus, to be essentially the same as the loss of biological activity measured after 12 months.

Furthermore, the pH measurements revealed that the pH value remained exceptionally stable over a period of up to 18 months. No trend towards higher or lower values was observed and all measured pH values remained within ±0.4 of the initial pH (see Table 3).

TABLE 3

Stability in terms of pH

STABILITY (pH)

| | | | Time (months) | | | | | |
|---|---|---|---|---|---|---|---|---|
| CONFIG. | Temperature | t = 0 (initial) | 1 | 3 | 6 | 9 | 12 | 18 |
| A | 2-8° C. | 6.8 | 6.8 | 6.8 | 6.9 | 6.7 | n.d. | 6.5 |
| B | | 6.5 | 6.9 | 6.9 | 6.8 | 6.9 | 6.6 | n.d. |
| A | 25° C. | 6.8 | 6.7 | 6.7 | 6.8 | 6.6 | 6.7 | n.d. |
| B | | 6.5 | 6.1 | 6.8 | 6.7 | 6.9 | n.d. | n.d. |

Moreover, the particle size measurements by Micro-Flow Imaging showed a low overall number of particles and no significant increase in the number of particles (see Table 4).

TABLE 4

Stability in terms of sub-visible particle count

STABILITY (sub-visible particle count (equal to or greater than 10 μm))

| | | | Time (months) | | | | | |
|---|---|---|---|---|---|---|---|---|
| CONFIG. | Temperature | t = 0 (initial) | 1 | 3 | 6 | 9 | 12 | 18 |
| A | 2-8° C. | 64 | 139 | 28 | 148 | 154 | 91 | 265 |
| B | | 472 | 126 | 100 | 90 | 369 | 97 | — |
| A | 25° C. | 64 | 192 | 60 | 210 | 163 | 280 | — |
| B | | 472 | 243 | 81 | 822 | 366 | 100 | — |

As can be seen from Table 4, the particle counts stay well below 1000/ml and in most cases even below 250/ml. Likewise, particle measurements by means of the Resonant Mass Measurement (RMM) method (using the ARCHIMEDES particle methodology system; Affinity Biosensors, Santa Barbara, CA, USA) and the Nanoparticle Tracking Analysis (using a NanoSight LM20 system; NanoSight, Amesbury, UK) lead to similar results and revealed no significant particle counts.

In conclusion, the results presented above show that liquid botulinum toxin formulations in prefilled plastic syringes are stable over a prolonged storage time (e.g., 12-24 months) at temperatures of 2-8° C. This finding was very surprising in view of the labile nature of botulinum toxin, which is known to be highly heat-labile and unstable at alkaline pH. This was all the more surprising since the botulinum toxin concentrations in prefilled syringes are exceptionally low and, thus, smallest absolute losses in the amount of active toxin will lead to large percentage changes.

Accordingly, the above results show that botulinum toxin can be formulated in a prefilled plastic syringe format, which offers advantages over glass syringes in terms of break resistance, decreased weight, increased flexibility for novel shapes of primary containers, improved dimensional tolerances, and absence of undesirable substances (e.g., adhesives). Moreover, compared to other botulinum toxin presentations, the prefilled syringe format enhances convenience and ease of handling, reduces medication errors, improves dosing accuracy, minimizes the risk of contamination, improves sterility assurance, and increases safety in administration.

The invention claimed is:

1. A prefilled plastic container comprising an aqueous botulinum toxin formulation, wherein the toxin activity is not reduced by more than 25%, relative to the initial toxin activity, upon storage of the prefilled container for 12 months at 5° C. or 3 months at 25° C.

2. The prefilled plastic container of claim 1, wherein the number of sub-visible particles of equal to or greater than 10 µm is below 1000/ml during storage for 6 to 24 months at 2° C. to 25° C.

3. The prefilled plastic container of claim 1, wherein the pH value is not increased or decreased by more than 10%, relative to the initial pH value, during storage of the prefilled container for 6 to 24 months at 2° C. to 25° C., or wherein the pH of the aqueous botulinum toxin formulation during storage is maintained in the range of 6.1 to 7.3, or both.

4. The prefilled plastic container of claim 1, wherein the botulinum toxin is present in the aqueous formulation at a concentration of 10 U/ml to 1000 U/ml.

5. The prefilled plastic container of claim 1, wherein the aqueous botulinum toxin formulation in the prefilled container does not contain a buffer.

6. The prefilled plastic container of claim 1, wherein the container is (i) a syringe, (ii) a vial, (iii) a carpule, or (iv) an ampoule.

7. The prefilled plastic container in the form of a prefilled plastic syringe of claim 6 comprising:
(a) a plastic syringe barrel including a proximal end and a distal end, and a generally cylindrical wall extending therebetween and defining a barrel lumen, the syringe barrel having a distally projecting tip with a fluid passage extending therethrough and communicating with the barrel lumen, wherein the generally cylindrical wall has an interior surface optionally coated with a barrier layer,
(b) a capping device having an outlet engaging portion sealingly engaging and closing the distal open outlet end of the syringe, wherein the outlet engaging portion is made of an elastomeric material that optionally has a coating on its surface, and
(c) a plunger rod assembly which extends into the proximal end of the syringe barrel and includes a plunger stopper in sliding fluid-tight engagement with the cylindrical wall of the barrel lumen, wherein the plunger stopper is made of an elastomeric material, which optionally has a coating on at least a portion of the plunger stopper contacting the aqueous botulinum toxin formulation during storage and/or injection.

8. The prefilled plastic container in the form of a prefilled plastic syringe of claim 7, wherein the barrier layer of the syringe barrel is a silicone-free layer or a silicone layer.

9. The prefilled plastic container in the form of a prefilled plastic syringe of claim 7, wherein the elastomeric material of the outlet engaging portion and/or the plunger stopper is selected from isoprene rubber (IS), butadiene rubber (BR), butyl rubber, halogenated butyl rubber, and styrene-butadiene rubber, and mixtures thereof, or wherein the optional coating on the outlet engaging portion and/or the plunger stopper is a crosslinked silicone coating or a fluoropolymer coating, or wherein the elastomeric material of the outlet engaging portion and/or the plunger stopper is selected from isoprene rubber (IS), butadiene rubber (BR), butyl rubber, halogenated butyl rubber, and styrene-butadiene rubber, and mixtures thereof, and the optional coating on the outlet engaging portion and/or the plunger stopper is a crosslinked silicone coating or a fluoropolymer coating.

10. A kit comprising a prefilled plastic container according to claim 1 and, optionally, instructions for use of said prefilled plastic container.

11. A method for the treatment of a disease or condition caused by or associated with hyperactive cholinergic innervation of muscles or exocrine glands in a patient, the method comprising locally administering an effective amount of botulinum toxin to a muscle or exocrine gland of the patient by injection using the prefilled plastic container according to claim 1.

12. A method for the cosmetic treatment of the skin, optionally for treating wrinkles of the skin and facial asymmetries, the method comprising locally administering an effective amount of botulinum toxin to a patient by intradermal, subdermal or subcutaneous injection using the prefilled plastic container according to claim 1.

* * * * *